United States Patent [19]

Uno et al.

[11] Patent Number: 4,749,703
[45] Date of Patent: Jun. 7, 1988

[54] CALCIUM ANTAGONIST PIPERAZINE DERIVATIVES, AND COMPOSITIONS THEREFOR

[75] Inventors: Hitoshi Uno, Takatsuki; Mikio Kurokawa; Fuminori Sato, both of Kobe; Naonobu Hatano, Takaishi, all of Japan

[73] Assignee: Dainippon Pharmaceutical Co., Ltd., Osaka, Japan

[21] Appl. No.: 855,849

[22] PCT Filed: Aug. 9, 1985

[86] PCT No.: PCT/JP85/00445

§ 371 Date: Apr. 10, 1986

§ 102(e) Date: Apr. 10, 1986

[87] PCT Pub. No.: WO86/01203

PCT Pub. Date: Feb. 27, 1986

[30] Foreign Application Priority Data

Aug. 10, 1984 [JP] Japan ................. 59-168532

[51] Int. Cl.$^4$ .................. A61K 31/38; A61K 31/495; C07D 241/02; C07D 401/04
[52] U.S. Cl. ..................... 514/253; 514/218; 514/252; 514/255; 540/575; 544/359; 544/360; 544/363; 544/380; 544/393
[58] Field of Search ............... 540/575; 544/359, 360, 544/363, 380, 393; 514/218, 252, 253, 255

[56] References Cited

U.S. PATENT DOCUMENTS 3,849,410 11/1974 Nakanishi et al. .................. 514/253
4,278,796 7/1981 Corvi-Mora ......................... 514/253
4,457,931 7/1984 Milani et al. ........................ 514/253

FOREIGN PATENT DOCUMENTS 46-2069  10/1971 Japan ................. 544/359
111583    9/1977 Japan ................. 544/359
55-3353   1/1980 Japan ................. 544/359
58-74666  5/1983 Japan ................. 544/359
96075     6/1983 Japan ................. 544/359
1284516   4/1971 United Kingdom ... 514/253
210533A   9/1982 United Kingdom ... 514/253

OTHER PUBLICATIONS

Thomas et al., J. of Cardiovascular Pharm. 6, 1170–1176, 1984, Raven Press, N.Y.
Meyer, Calcium Antagonists and Cardiovascular Disease, Raven Press, N.Y., 1984, pp. 165–173.
Rajsner et al., CA vol. 101, 1984, 101:54944h, p. 608.

*Primary Examiner*—Richard A. Schwartz
*Assistant Examiner*—J. G. Mullins
*Attorney, Agent, or Firm*—Scully, Scott, Murphy & Presser

[57] ABSTRACT

Compounds of the formula:

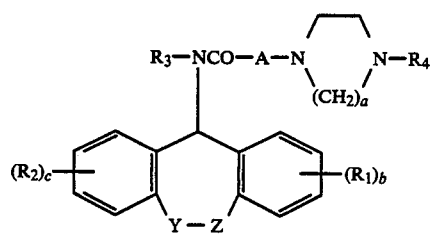

wherein A means an alkylene; Y—Z means

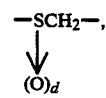

—CH=CH—, —CH$_2$CH$_2$—, or

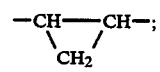

$R_1$ and $R_2$ are each a substituent; $R_3$ is hydrogen atom, alkyl, or alkoxy; $R_4$ is phenyl, phenylalkyl, phenylalkenyl, diphenylmethyl, naphthyl, thiazolyl, optionally substituted pyridyl, optionally substituted pyrimidinyl, quinolyl, benzoylalkyl, benzoyl, furoyl, thenoyl, phenyloxycarbonyl, phenyloxysulfonyl, or phenylsulfonyl; a is 2 or 3, b and c are each 1 or 2, and d is an integer of 0 to 2, provided that the phenyl, phenyl moiety and naphthyl may optionally be substituted, and a pharmaceutically acceptable salt thereof, process for the preparation thereof, and pharmaceutical composition containing the same. The compounds and salt thereof show potent calcium antagonistic activity and are useful for prophylaxis and treatment of hypertension and/or ischemic heart disease.

20 Claims, No Drawings

CALCIUM ANTAGONIST PIPERAZINE DERIVATIVES, AND COMPOSITIONS THEREFOR

TECHNICAL FIELD

The present invention relates to novel tricyclic or tetracyclic compounds having ω-[4-substituted-1-(homo)piperazinyl]alkanoylamino group which have a calcium antagonistic activity and hence are useful as a medicament, a process for preparing the compounds, and a pharmaceutical composition containing the compound as an active ingredient.

BACKGROUND ART

With recent elucidation of physiological roles of calcium, various calcium antagonists having various chemical structures have been studied and have been come into the market. There have now been used the calcium antagonists such as nifedipine, diltiazem hydrochloride, etc. for the prophylaxis and treatment of various diseases such as ischemic heart disease, hypertension and the like. These medicaments have, however, comparatively short duration of action, and hence, it has been desired to find a medicament having more prolonged activity.

As far as the present inventors know, there is no report that a tricyclic or tetracyclic compound having ω-[4-substituted-1-(homo)piperazinyl]alkanoylamino group has a calcium antagonistic activity.

The present inventors have intensively studied in order to obtain novel compounds having a chemical structure different from the known calcium antagonists and having superior activity to the latter, and have found that tricyclic or tetracyclic compounds having ω-[4-substituted-1-(homo)piperazinyl]alkanoylamino group show potent calcium antagonistic activity when they satisfy the following conditions:

(i) the substituent at 4-position of the (homo)piperazinyl group contains at least one aromatic hydrocarbon group or aromatic heterocyclic group, and (ii) the middle ring of the tricyclic or tetracyclic group is a seven-membered ring, and further that some of them show more prolonged antihypertensive activity than that of the commercially available calcium antagonists.

DISCLOSURE OF INVENTION

The present invention provides compounds of the formula (I):

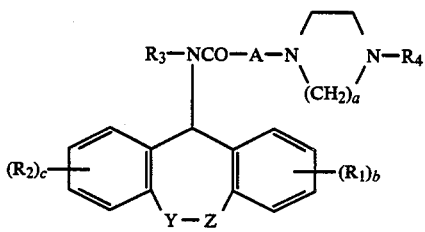

wherein A means a $C_{1-10}$ alkylene; Y-Z means

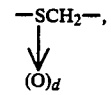

—CH=CH—, —CH$_2$CH$_2$—, or

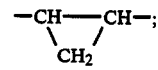

$R_1$ groups are the same or different and are each hydrogen atom, a halogen atom, a $C_{1-6}$ alkyl, a $C_{1-6}$ alkoxy, a $C_{1-6}$ alkylthio, or cyano; $R_2$ groups are the same or different and are each hydrogen atom, a halogen atom, a $C_{1-6}$ alkyl, a $C_{1-6}$ alkoxy, a $C_{1-6}$ alkylthio, or cyano; $R_3$ is hydrogen atom, a $C_{1-6}$ alkyl, or a $C_{1-6}$ alkoxy; $R_4$ is phenyl, a phenyl-$C_{1-10}$ alkyl wherein the alkyl moiety may optionally be substituted by one hydroxy, a phenyl-$C_{3-5}$ alkenyl, diphenylmethyl, naphthyl, thiazolyl, a pyridyl which may optionally be substituted by a $C_{1-6}$ alkoxycarbonyl, a pyrimidinyl which may optionally be substituted by a $C_{1-6}$ alkyl, quinolyl, a benzoyl-$C_{1-5}$ alkyl, benzoyl, furoyl, thenoyl, phenyloxycarbonyl, phenyloxysulfonyl, or phenylsulfonyl; a is 2 or 3, b and c are each 1 or 2, and d is an integer of 0 to 2, provided that the phenyl, phenyl moiety and naphthyl in the above definition may optionally be substituted by one or two members selected from the group consisting of a halogen atom, hydroxy, nitro, a $C_{1-6}$ alkyl, trifluoromethyl and a $C_{1-6}$ alkoxy, and when two substituents are contained, both may be the same or different, and a pharmaceutically acceptable salt thereof, a process of the preparation of the compounds, and a pharmaceutical compposition containing the compounds as an active ingredient.

The pharmaceutically acceptable salts of the compounds (I) include, for example, inorganic acid addition salts (e.g. hydrochloride, hydrobromide, hydroiodide, sulfate, phosphate, etc.) and organic acid addition salts (e.g. oxalate, maleate, fumarate, lactate, malate, citrate, tartrate, benzoate, methanesulfonate, etc.) The compounds (I) and salts thereof may optionally be present in the form of a hydrate or a solvate, and these hydrate and solvate are also included in the present invention.

Besides, the compounds (I) may have one or more asymmetric carbons and occasionally have one asymmetric sulfur, and hence, they may be present in the form of a stereoisomer. These stereoisomers, a mixture thereof or a racemic compound thereof are also included in the present invention.

The terms for the groups used in the present specification have the following meanings.

The alkylene or alkyl group, or alkyl or alkenyl moiety in the alkoxy, alkylthio, phenylalkyl, phenylalkenyl, or alkoxycarbonyl includes straight or branched chain groups, preferably straight chain groups. The alkylene group includes, for example, methylene, ethylene, trimethylene, tetramethylene, pentamethylene, hexamethylene, heptamethylene, and the like. The halogen atom includes fluorine, chlorine, bromine and iodine, preferably fluorine, chlorine and bromine, particularly preferably fluorine. The alkyl group includes, for example, methyl, ethyl, propyl, isopropyl, butyl, and the like, preferably methyl. The alkoxy group includes, for example, methoxy, ethoxy, propoxy, isopropoxy, and the like, preferably methoxy. The alkylthio group includes, for example, methylthio, ethylthio, propylthio, isopropylthio, and the like, preferably methylthio. The optionally substituted phenyl group includes, for example, phenyl, 2-, 3- or 4-fluorophenyl, 2-, 3- or 4-chlorophenyl, 2-, 3- or 4-hydroxyphenyl, 2-, 3- or 4-nitrophenyl, 2-, 3- or 4-methylphenyl, 2-, 3- or 4-trifluoromethylphenyl, 2-, 3- or 4-methoxyphenyl, 3,4-dimethoxyphenyl, and the like. The phenylalkyl group wherein the alkyl moiety may optionally be substituted by one hydroxy includes, for example, benzyl, phenethyl, 3-phenylpropyl, 4-phenylbutyl, 5-phenylpentyl, 2-hydroxy-2-phenylethyl, and 2-hydroxy-3-phenylpropyl, and the phenyl moiety may have the same substituent as specified above. The optionally substituted phenylalkenyl group includes, for example, cinnamyl and a cinnamyl wherein the phenyl moiety has the same substituent as specified above. The optionally substituted diphenylmethyl or naphthyl group includes, for example, diphenylmethyl or naphthyl which may optionally have the same substituents as specified above on the phenyl or naphthyl ring.

The preferred compounds in the present invention are the compounds of the formula (I) wherein A is $-(CH_2)_n-$; n is an integer of 1 to 5; Y—Z is

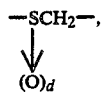

$-CH=CH-$, $-CH_2CH_2-$ or

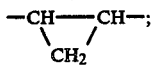

one of $R_1$ and $R_2$ is hydrogen atom and the other is hydrogen atom, a halogen atom, methyl, ethoxy, methylthio, or cyano; $R_3$ is hydrogen atom; $R_4$ is phenyl, a phenyl which has a substituent selected from the group consisting of a halogen atom, hydroxy, nitro, methyl, trifluoromethyl and methoxy, a phenyl-$C_{1-5}$ alkyl, a phenyl-$C_{1-5}$ alkyl in which the phenyl moiety has a substituent selected from the group consisting of a halogen atom, methyl and trifluoromethyl, cinnamyl, pyridyl, pyrimidinyl, or quinolyl; a is 2; b and c are each 1; and d is an integer of 0 to 2, and pharmaceutically acceptable salts thereof.

More preferred compounds are the compounds of the formula (I) wherein A is ethylene, trimethylene, or tetramethylene; Y—Z is

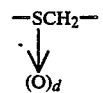

or $-CH=CH-$; one of $R_1$ and $R_2$ is hydrogen atom and the other is hydrogen atom, fluorine, or methyl; $R_3$ is hydrogen atom; $R_4$ is phenyl, fluorophenyl, chlorophenyl, methylphenyl, trifluoromethylphenyl, methoxyphenyl, benzyl, fluorobenzyl, chlorobenzyl, cinnamyl, 2-pyridyl, 2-pyrimidinyl, or 2-quinolyl; a is 2; b and c are each 1; and d is an integer of 0 to 2, and pharmaceutically acceptable salts thereof.

Particularly preferred compounds are the compounds of the formula (I) wherein A is trimethylene; Y—Z is

or $-CH=CH-$; one of $R_1$ and $R_2$ is hydrogen atom and the other is hydrogen atom, fluorine, or methyl; $R_3$ is hydrogen atom; $R_4$ is phenyl or 4-fluorophenyl; a is 2; b and c are each 1; and d is an integer of 0 to 2, and pharmaceutically acceptable salts thereof.

Specific examples of the particularly preferred compounds are the following compounds and pharmaceutically acceptable salts thereof, and the first five compounds of them and pharmaceutically acceptable salts thereof are specifically preferred in view of the prolonged antihypertensive activity thereof.

11-[4-[4-(4-fluorophenyl)-1-piperazinyl]butyrylamino]-6,11-dihydrodibenzo[b,e]thiepin, 11-[4-[4-(4-fluorophenyl)-1-piperazinyl]butyrylamino]-2-methyl-6,11-dihydrodibenzo[b,e]thiepin, 3-fluoro-11-[4[4-(4-fluorophenyl)-1-piperazinyl]-butyrylamino]-6,11-dihydrodibenzo[b,e]thiepin, 11-[4-[4-(4-fluorophenyl)-1-piperazinyl]butyrylamino]-6,11-dihydrodibenzo[b,e]thiepin-5-oxide, 11-[4-[4-(4-fluorophenyl)-1-piperazinyl]butyrylamino]-6,11-dihydrodibenzo[b,e]thiepin-5,5-dioxide, 11-[4-(4-phenyl-1-piperazinyl)butyrylamino]-6,11-dihydrodibenzo[b,e]thiepin, and 5-[4-[4-(4-fluorophenyl)-1-piperazinyl]butyrylamino]-5H-dibenzo[a,d]cycloheptene.

The compounds of the present invention can be prepared, for example, by the following processes.

Process (a)

The compounds of the formula (I) can be prepared by reacting a compound of the formula (II):

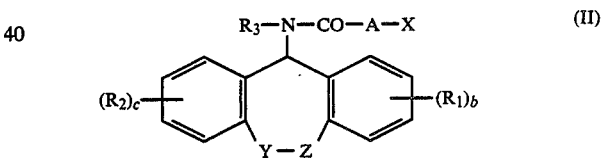

wherein A, Y—Z, $R_1$, $R_2$, $R_3$, b and c are as defined above, and X is a residue of a reactive ester of an alcohol, with a compound of the formula (III):

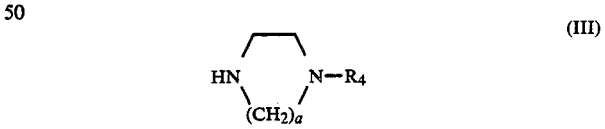

wherein $R_4$ and a are as defined above.

In the formula (II), the residue of reactive ester of an alcohol as defined for X includes, for example, a halogen atom such as chlorine, bromine or iodine, a lower alkylsulfonyloxy such as methanesulfonyloxy or ethanesulfonyloxy, an arylsulfonyloxy such as benzenesulfonyloxy, p-toluenesulfonyloxy or m-nitrobenzenesulfonyloxy.

The reaction of the compound (II) and the compound (III) is carried out in a suitable solvent or without using any solvent. Suitable examples of the solvent are aromatic hydrocarbons (e.g. benzene, toluene, xylene), ketones (e.g. methyl ethyl ketone), ethers (e.g. tetrahydrofuran, dioxane), alcohols (e.g. ethanol, isopropyl alcohol), acetonitrile, dimethylformamide, and the like. These solvents may be used alone or in combination of two or more thereof. The reaction is preferably carried out in the presence of a base. Suitable examples of the base are alkali metal bicarbonates (e.g. sodium bicarbonate, potassium bicarbonate), alkali metal carbonates (e.g. sodium carbonate, potassium carbonate), and organic bases (e.g. triethylamine, tri-n-butylamine, diisopropylethylamine, N-methylmorpholine, dicyclohexylamine). The compounds (III) may be used in an excess amount to serve as the base. Besides, when the compound of the formula (II) wherein X is chlorine or bromine is used, the reaction can proceed more smoothly by adding an alkali metal iodide such as sodium iodide or potassium iodide to the reaction system. The reaction is usually carried out at a temperature of from about 20° C. to about 200° C., preferably of from about 70° C. to about 150° C., and the reaction period of time is usually in the range of from one hour to 24 hours.

Among the starting compounds (II), the compounds of the formula (II) wherein Y—Z is —SCH$_2$—, —CH=CH—, —CH$_2$CH$_2$— or

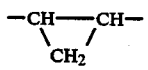

can be prepared, for example, by the reaction of a compound of the formula (IV') and an acid chloride of the formula (V) under conventional amidation conditions as shown in the following reaction scheme. The starting compound (IV') can be prepared by a known process [cf. Collection Czechoslov. Chem. Commun., 45, 517–528 (1980) as to the compounds (IV') wherein Y—Z is —SCH$_2$—; Chem. Abstr., 66, 2426a (1967) as to the compounds (IV') wherein Y—Z is —CH=CH—; J. Med. Chem., 6, 255–261 (1963) as to the compounds (IV') wherein Y—Z is —CH$_2$CH$_2$—; and J. Med. Chem., 17, 72–75 (1974) and Collection Czechoslov. Chem. Commun., 45, 517–528 (1980) as to the compounds (IV') wherein Y—Z is

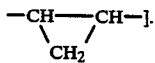

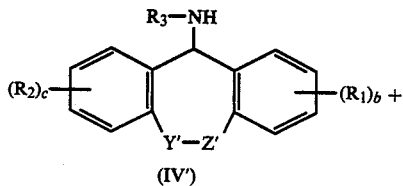

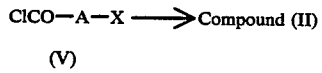

wherein A, R$_1$, R$_2$, R$_3$, b, c and X are as defined above, and Y'—Z' means —SCH$_2$—, —CH=CH—, —CH$_2$CH$_2$— or

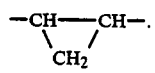

The compounds of the formula (II) wherein Y—Z is

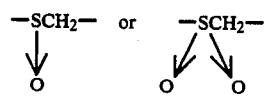

can be prepared by oxidizing a compound of the formula (II) wherein Y—Z is —SCH$_2$— by a conventional method.

Process (b)

The compounds of the formula (I) can be prepared by reacting a compound of the formula (IV):

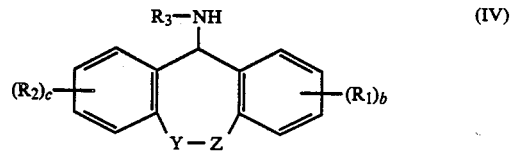

wherein Y—Z, R$_1$, R$_2$, R$_3$, b and c are as defined above, with a compound of the formula (VI):

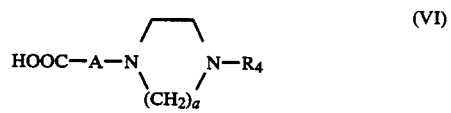

wherein A, R$_4$ and a are as defined above, or a reactive derivative thereof.

The reactive derivative of the compound (VI) includes, for example, activated esters, acid anhydrides and acid halides (particularly acid chloride). Suitable examples of the activated esters are p-nitrophenyl ester, 2,4,5-trichlorophenyl ester, pentachlorophenyl ester, cyanomethyl ester, N-hydroxysuccinimide ester, N-hydroxyphthalimide ester, N-hydroxy-5-norbornene-2,3-dicarboximide ester, N-hydroxypiperidine ester, 8-hydroxyquinoline ester, 2-hydroxyphenyl ester, 2-hydroxy-4,5-dichlorophenyl ester, 2-hydroxypyridine ester, 2-pyridylthio ester, and the like. The acid anhydrides include symmetric acid anhydrides and mixed acid anhydrides. Suitable examples of the mixed acid anhydrides are mixed acid anhydrides with carbonic acid monoalkyl esters (e.g. carbonic acid monoethyl ester, carbonic acid monoisobutyl ester), mixed acid anhydrides with carbonic acid monoaryl esters (e.g. carbonic acid monophenyl ester), mixed acid anhydrides with alkanoic acids (e.g. isovaleric acid, pivalic acid), and the like.

When the compounds (VI) are used, the reaction can be carried out in the presence of a condensation agent, such as dicyclohexylcarbodiimide, 1-ethyl-3-(3-dimethylaminopropyl)carbodiimide hydrochloride, carbonyldiimidazole, 1-ethoxycarbonyl-2-ethoxy-1,2-dihydroquinoline, and the like. When dicyclohexylcarbodiimide is used as the condensation agent, the reaction may be carried out by adding N-hydroxysuccinimide, 1-hydroxybenzotriazole, 3-hydroxy-4-oxo-3,4-dihydro-1,2,3-benzotriazine, N-hydroxy-5-norbornene-2,3-dicarboximide, and the like to the reaction system.

The reaction of the compound (IV) and the compound (VI) or a reactive derivative thereof is usually carried out in a solvent. Suitable solvent is selected in accordance with the kinds of the starting compounds, and includes, for example, aromatic hydrocarbons (e.g. benzene, toluene, xylene), ethers (e.g. diethyl ether, tetrahydrofuran, dioxane), halogenated hydrocarbons (e.g. methylene chloride, chloroform), ethyl acetate, acetonitrile, dimethylformamide, dimethylsulfoxide, water, and the like. These solvents may be used alone or in combination of two or more thereof. The reaction may optionally be carried out in the presence of a base. Suitable examples of the base are the same as described above as to the process (a). The reaction temperature may vary in accordance with the kinds of the starting compounds, but is usually in the range of from about −40° C. to about 150° C., preferably from about −20° C. to about 80° C., and the reaction period of time is usually in the range of from one hour to 24 hours.

The starting compounds of the formula (IV) wherein Y—Z is —SCH$_2$—, —CH=CH—, —CH$_2$CH$_2$— or

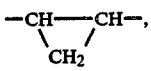

can be prepared by the method disclosed in literatures as mentioned in the above process (a). The compounds of the formula (IV) wherein Y—Z is

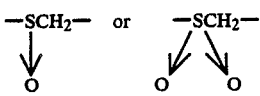

can be prepared by oxidizing in a usual manner an appropriate intermediate for a compound of the formula (IV) wherein Y—Z is —SCH$_2$—, followed by converting the product into the desired compound.

Process (c)

The compounds of the formula (I) wherein Y—Z is —CH=CH— can be prepared by reacting a compound of the formula (VII):

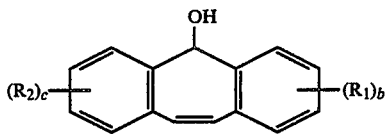

wherein R$_1$, R$_2$, b and c are as defined above, with a compound of the formula (VIII):

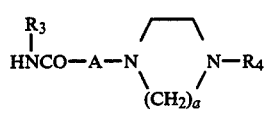

wherein A, R$_3$, R$_4$ and a are as defined above.

The reaction of the compound (VII) and the compound (VIII) is usually carried out in an acidic solvent such as formic acid or acetic acid. The reaction temperature is usually in the range of from about 20° C. to about 200° C., preferably from about 40° C. to about 120° C., and the reaction period of time is usually in the range of from one hour to 24 hours.

The starting compound (VII) is commercially available or can be prepared by reducing the corresponding oxo compound in a usual manner. The oxo compound can be prepared according to the method disclosed in J. Am. Chem. Soc., 73, 1673–1678 (1951) or J. Med. Cehm., 20, 1557–1562 (1977).

Process (d)

The compounds of the formula (I) wherein Y—Z is

can be prepared by oxidizing a compound of the formula (I'):

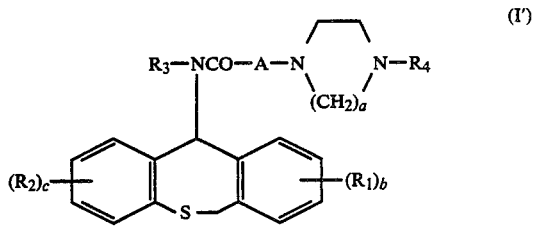

wherein A, R$_1$, R$_2$, R$_3$, R$_4$, a, b and c are as defined above.

The reaction is usually carried out by treating the compound (I') with an oxidizing agent in a suitable solvent. The oxidizing agent includes inorganic peroxides (e.g. sodium metaperiodate, hydrogen peroxide) and organic peroxides (e.g. peracetic acid, perbenzoic acid, m-chloroperbenzoic acid, monoperphthalic acid). The amount of the oxidizing agent used is a stoichiometric quantity, based on the amount of the compound (I'), or a slightly excess amount. The solvent is selected in accordance with the kinds of the oxidizing agents, and includes, for example, aromatic hydrocarbons (e.g. benzene, toluene), halogenated hydrocarbons (e.g. methylene chloride, chloroform, ethylene chloride), ethers (e.g. diethyl ether, dioxane), alcohols (e.g. methanol, ethanol), water, and the like. The reaction temperature may vary in accordance with the kinds of the oxidizing agents, but is usually in the range of from about 0° C. to about 100° C., and the reaction period of time is usually in the range of from 30 minutes to 6 hours.

The starting compound (I') can be prepared, for example, by the above-mentioned process (a) or (b).

The compounds (I) prepared by the above processes can be isolated and purified by conventional techniques, such as chromatography, recrystallization or re-precipitation.

The compounds (I) may be obtained in the form of a free base, salt, hydrate or solvate depending on the kinds of the starting compounds, reaction and treating conditions, and the like. The salt can be converted into a free base by treating it with a base such as an alkali metal hydroxide in a usual manner. On the other hand, the free base may be converted into a salt by treating it by various acids in a usual manner. For instance, when a compound of the formula (I) is reacted with an appropriate acid in a solvent and the reaction product is purified by recrystallization or reprecipitation, there is obtained a salt of the compound (I). The solvent includes, for example, chloroform, methanol, ethanol, isopropyl alcohol, water, and the like. The acid is usually used in an amount of one to about three moles to one mole of the compound (I). The reaction temperature is usually in the range of about 10° C. to about 80° C.

The pharmacological activities of the compounds of the present invention are illustrated by the results of the following experiments, which were carried out for the representative compounds of the present invention, using commercially available calcium antagonists, i.e. diltiazem hydrochloride and nifedipine as reference compounds.

TEST 1

Calcium Antagonistic Activity

The test was carried out according to the method of Godfraind et al. [cf. Br. J. Pharmac., 36 549–560 (1969)].

Male Wistar strain rats, weighing about 300 g, were killed by a blow on the head. The thoracic aorta was removed and cut into a spiral strip 3-4 mm in width and about 30 mm in length. The preparation was suspended in 10 ml of Krebs bicarbonate solution kept at 37° C. and gassed with 95% $O_2$-5% $CO_2$, and resting tension was added to 1 g. Contractile responses of the aorta were recorded on an ink-writing oscillograph with a tension-displacement transducer.

First, the solution in which the aortic strip had been suspended was replaced with a calcium-free Krebs bicarbonate solution with higher concentration of $K^+$ to cause depolarization and then $CaCl_2$ was added cumulatively to make $Ca^{++}$ dose-response curve. Second, the same experiment was carried out in the presence of test compound to make $Ca^{++}$ dose-response curve. The $pA_2$ value of calcium antagonistic activity of the test compound was calculated according to the method of Van Rossum [cf. Arch. int. Pharmacodyn., 143, 299–330 (1963)]. The $pA_2$ value is defined as the negative logarithm of the molar concentration of the test compound which will produce a two-fold shift of the $Ca^{++}$ dose-response curve (in the absence of test compound) toward higher concentration.

The results are shown in Table 1. The values in the table are represented as a mean value ± a standard error from 3-6 strips of the aorta.

TABLE 1

| Test compound | Calcium antagonistic activity $pA_2$ | Test compound | $pA_2$ |
|---|---|---|---|
| 1(1)* | 8.71 ± 0.08 | 70 | 8.38 ± 0.05 |
| 2(1) | 8.37 ± 0.05 | 71 | 8.18 ± 0.08 |
| 3(1) | 8.57 ± 0.06 | 72 | 7.85 ± 0.09 |
| 4(1) | 8.45 ± 0.05 | 73 | 7.69 ± 0.09 |
| 5(1) | 8.75 ± 0.11 | 75 | 7.44 ± 0.08 |
| 6(1) | 8.76 ± 0.03 | 76 | 7.88 ± 0.17 |
| 7(1) | 8.23 ± 0.14 | 77 | 7.98 ± 0.08 |
| 8(1) | 8.54 ± 0.06 | 79(1) | 8.98 ± 0.08 |
| 9(1) | 8.54 ± 0.08 | 80(1) | 8.32 ± 0.06 |
| 10(1) | 8.55 ± 0.11 | 81(1) | 8.43 ± 0.06 |
| 11(1) | 8.46 ± 0.08 | 82(1) | 8.61 ± 0.07 |
| 12 | 8.69 ± 0.06 | 83 | 8.10 ± 0.04 |
| 13 | 8.43 ± 0.07 | 84(1) | 8.09 ± 0.07 |
| 14 | 8.49 ± 0.09 | 85(1) | 8.22 ± 0.08 |
| 15 | 8.37 ± 0.09 | 86(1) | 7.96 ± 0.08 |
| 16 | 8.47 ± 0.12 | 87 | 8.05 ± 0.22 |
| 17 | 8.48 ± 0.12 | 88 | 8.00 ± 0.10 |
| 18 | 8.17 ± 0.04 | 89(1) | 8.56 ± 0.13 |
| 19 | 8.55 ± 0.04 | 90(1) | 8.35 ± 0.06 |
| 20 | 8.50 ± 0.06 | 91 | 8.18 ± 0.08 |
| 21 | 8.64 ± 0.01 | 92 | 8.57 ± 0.06 |
| 22 | 8.48 ± 0.17 | 93 | 8.71 ± 0.04 |
| 23 | 8.48 ± 0.04 | 94 | 8.46 ± 0.10 |
| 24 | 8.30 ± 0.14 | 95 | 7.96 ± 0.05 |
| 25 | 8.75 ± 0.18 | 96 | 8.68 ± 0.08 |
| 26 | 8.39 ± 0.19 | 97 | 8.54 ± 0.09 |
| 27 | 9.28 ± 0.08 | 98 | 8.81 ± 0.09 |

TABLE 1-continued

| Test compound | Calcium antagonistic activity $pA_2$ | Test compound | $pA_2$ |
|---|---|---|---|
| 28 | 8.10 ± 0.17 | 99 | 8.48 ± 0.08 |
| 30 | 7.95 ± 0.10 | 100 | 8.27 ± 0.18 |
| 32 | 8.37 ± 0.19 | 101 | 8.26 ± 0.04 |
| 33 | 8.44 ± 0.06 | 102 | 7.45 ± 0.11 |
| 34 | 8.44 ± 0.21 | 103 | 8.28 ± 0.19 |
| 35 | 8.32 ± 0.10 | 104 | 8.30 ± 0.18 |
| 36 | 8.19 ± 0.12 | 105 | 7.69 ± 0.28 |
| 37 | 8.13 ± 0.02 | 106 | 7.71 ± 0.06 |
| 38 | 8.29 ± 0.10 | 107 | 8.52 ± 0.07 |
| 39 | 8.42 ± 0.23 | 108 | 8.53 ± 0.15 |
| 40 | 8.42 ± 0.07 | 109 | 8.44 ± 0.06 |
| 41 | 8.64 ± 0.05 | 110 | 7.85 ± 0.09 |
| 42 | 8.59 ± 0.16 | 111 | 8.72 ± 0.20 |
| 43 | 8.47 ± 0.05 | 112 | 8.93 ± 0.12 |
| 44 | 8.17 ± 0.06 | 113 | 7.96 ± 0.15 |
| 45 | 8.93 ± 0.03 | 114 | 8.27 ± 0.09 |
| 46 | 7.80 ± 0.13 | 115 | 7.51 ± 0.08 |
| 47 | 8.23 ± 0.14 | 116 | 7.83 ± 0.05 |
| 48 | 8.30 ± 0.01 | 117 | 8.28 ± 0.09 |
| 49 | 7.49 ± 0.04 | 118 | 8.08 ± 0.04 |
| 50 | 8.31 ± 0.09 | 123 | 8.41 ± 0.04 |
| 51 | 7.85 ± 0.12 | 124 | 7.52 ± 0.05 |
| 52 | 7.68 ± 0.06 | 125 | 7.83 ± 0.03 |
| 53 | 7.72 ± 0.02 | 126 | 8.41 ± 0.02 |
| 54 | 7.97 ± 0.06 | 127 | 7.69 ± 0.07 |
| 55 | 7.55 ± 0.10 | 128 | 7.45 ± 0.12 |
| 56 | 7.79 ± 0.09 | 131(1) | 8.23 ± 0.05 |
| 60 | 7.74 ± 0.08 | 132(1) | 8.03 ± 0.06 |
| 61 | 8.81 ± 0.15 | 133(1) | 7.99 ± 0.06 |
| 62 | 8.12 ± 0.05 | 134 | 7.44 ± 0.09 |
| 63 | 7.91 ± 0.18 | 135 | 8.22 ± 0.17 |
| 64 | 7.81 ± 0.17 | 136 | 7.80 ± 0.09 |
| 65 | 7.60 ± 0.20 | 137 | 7.93 ± 0.04 |
| 67 | 7.59 ± 0.07 | 138 | 7.81 ± 0.11 |
| 68 | 7.57 ± 0.08 | 140 | 8.20 ± 0.13 |
| 69(1) | 8.50 ± 0.29 | 141 | 7.94 ± 0.11 |
| Diltiazem hydrochloride | 7.42 ± 0.05 | Nifedipine | 9.83 ± 0.08 |

*It means the compound of Ex. 1(1) (hereinafter the same)

As shown in Table 1 most of the compounds of the present invention tested exhibited much more potent calcium antagonistic activity than diltiazem hydrochloride, while weaker than nifedipine.

TEST 2

Antihypertensive activity in spontaneously hypertensive rats (SHR)

The animals used were male SHR [Okamoto and Aoki strain; cf. Jap. Circul. J., 27, 282–293 (1963)], 18–26 weeks of age, bred in Research Laboratories of Dainippon Pharmaceutical Co., Ltd. The rats were implanted with an abdominal aortic cannula (produced by Clay Adams Co., Ltd., U.S.A., polyethylene tube, PE-50) according to the method of Weeks et al. [cf. Proc. Soc. Exp. Biol. Med., 104, 646–648 (1960)]. The other end of the cannula was exposed through the skin on the back of the neck and fixed. After 1 to 4 days, the aortic cannula was connected to a pressure transducer (produced by Nihon Koden Co., Ltd., Japan; Model MP-4T), and conscious blood pressure was measured by direct method. On the day of the experiment, the blood pressure was measured for one hour prior to dosing. The test compound, suspended in 0.5% aqueous tragacanth solution, was administered orally at a volume of 3.0 ml/kg and the blood pressure was measured continuously for 5 hours.

Table 2 shows the initial blood pressures of the test animals, the time at which the maximum hypotensive effect was observed (peak time), and the changes of blood pressure both at the peak time and 5 hours after the administration. The extent of hypotensive activity at 5 hours is considered to be a good measure for evaluating the duration of the action of the test compounds. The changes of blood pressure are expressed by the mean pressure calculated from the values of systolic and diastolic pressure.

TABLE 2

| Test compound | Dose (mg/kg, p.o.) | No. of animal | Initial blood pressure (mmHg) | Peak time | Change of blood pressure, mmHg (%) peak time | Change of blood pressure, mmHg (%) 5 hrs. after administn. |
|---|---|---|---|---|---|---|
| 1(3)* | 30 | 6 | 162 | 5 hr | −21(−13) | −21(−13) |
| 2(3) | 30 | 5 | 164 | 4 hr | −21(−13) | −20(−12) |
| 42 | 30 | 5 | 151 | 4 hr | −22(−14) | −21(−14) |
| 136 | 30 | 5 | 162 | 5 hr | −19(−12) | −19(−12) |
| 138 | 30 | 3 | 158 | 5 hr | −21(−14) | −21(−14) |
| Diltiazem hydrochloride | 30 | 7 | 148 | 20 min | −7(−5) | −5(−3) |
|  | 50 | 5 | 156 | 20 min | −20(−13) | −4(−3) |
| Nifedipine | 3 | 5 | 145 | 30 min | −25(−17) | −10(−7) |

*It means the compound of Ex. 1(3) (hereinafter the same)

As shown in Table 2, the compounds obtained in Examples 1(3), 2(3), 42, 136 and 138 exhibited a maximum hypotensive effect (a 12–14% decrease compared with the initial blood pressure) at 4–5 hours after an oral administration of 30 mg/kg. On the other hand, diltiazem hydrochloride did not reduce significantly blood pressures at the same dose, while it showed a maximum effect (13% decrease) at 20 minutes after an oral administration of 50 mg/kg. Nifedipine produced a maximum hypotensive effect (17% decrease) at 30 minutes after an oral administration of 3 mg/kg. At 5 hours after dosing, the compounds of the present invention showed a maximum hypotensive effect or a comparable effect to it, but diltiazem hydrochloride and nifedipine showed only 3% and 7% decrease compared with the initial blood pressure, respectively. These data suggest that the duration of antihypertensive activity of the compounds of the present invention is much longer than that of the commercially available calcium antagonists.

TEST 3

Effect in rat of experimental model of ischemic heart disease (1) Preventive effect on vasopressin-induced ST depression (effect in experimental model of angina pectoris)

The test was carried out according to the method of Hatano et al. [cf. Pharmacometrics, 19, 311–317 (1980)].

Male Donryu strain rats, weighing 130–180 g, were anesthetized with 60 mg/kg (i.p.) of sodium pentobarbital. Lead II electrocardiogram was recorded. The ST depression produced with 0.2 IU/kg (i.v.) of vasopressin was recorded at intervals of a given period for 5 minutes after the administration of vasopressin. The test compound, suspended in 0.5% aqueous tragacanth solution, was administered orally 1, 3, 5 and 7 hours before the administration of vasopressin. The amplitude of ST depression was measured by means of the computer, and the data were analyzed statistically by two-dimensional analysis between the control group and the treated group to evaluate the effect of the test compound. Each group of 5 rats was used for each dose of the test compound. The results are shown in Table 3.

TABLE 3

Preventive effect on vasopressin-induced ST depression

| Test compound | Dose (mg/kg, p.o.) | Preventive effect on ST depression Time following administration (hour) 1 | 3 | 5 | 7 |
|---|---|---|---|---|---|
| 1(3)* | 30 |  |  |  | + |
|  | 10 | + |  | + | − |
|  | 3 | + |  | − |  |
| 2(3) | 30 |  |  |  | + |
|  | 10 | + | + | + | − |
|  | 3 | − | − | − | − |
| 79(3) | 30 |  |  |  | + |
|  | 10 | + |  | + | − |
|  | 3 | + | + | − |  |
| Diltiazem hydrochloride | 30 | + |  | + | − |
|  | 10 | + | + |  | − |
|  | 3 | − | − |  |  |
| Nifedipine | 0.1 | + | − | − |  |
|  | 0.01 | − | − |  |  |

*It means the compound of Ex. 1(3) (hereinafter the same)
+: Significantly different from vehicle control (P < 0.05)
−: No significant difference As shown in Table 3, the compounds obtained in Examples 1(3), 2(3) and 79(3) exhibited more prolonged preventive effect on the ST depression than diltiazem hydrochloride.

(2) Preventive effect on methacholine-induced ST elevation (effect in experimental model of variant angina)

The test was carried out according to the method of Sakai et al. [cf. J. Pharmacol. Methods, 5, 325–336 (1981)].

Male SD strain rats, weighing about 500 g, were anesthetized with 60 mg/kg (i.p.) of sodium pentobarbital. Lead II electrocardiogram was recorded. The ST elevation was produced with 8.0 μg of metacholine given into the coronary aorta through the cannula inserted from the right carotid artery. The test compound, dissolved in 5% ethanol-physiological saline solution, was administered intravenously. The amplitude of ST elevation was measured by means of the computer 0.5, 5 and 10 minutes after the administration of the test compound and afterward at intervals of 10-minute. The effect of the test compound was evaluated by comparing the amplitude of ST elevation after administration of the test compound with that before the administration. Each group of 5 rats was used for each dose of the test compound.

The results are shown in Table 4. The abbreviation M in the table represents metacholine.

TABLE 4

Preventive effect on methacholine-induced ST elevation

| Test compd. | Dose (mg/kg, i.v.) | ST in no administn. of M (mV + S.E.) | ST elevation ($\Delta$mV ± S.E.) Administn. of only M (8 µg) | Administn. of M (8 µg) after administn. of test compd. (at peak time: min) |
|---|---|---|---|---|
| 1(3)*** | 0.1 | −0.16 ± 0.02 | +0.20 ± 0.02 | +0.14 ± 0.02(0.5) |
|  | 0.3 | −0.17 ± 0.02 | +0.20 ± 0.02 | +0.09 ± 0.02**(5) |
|  | 1.0 | −0.19 ± 0.04 | +0.24 ± 0.02 | +0.09 ± 0.01**(0.5) |
| 2(3) | 0.1 | −0.15 ± 0.08 | +0.27 ± 0.04 | +0.19 ± 0.05(5) |
|  | 0.3 | −0.17 ± 0.07 | +0.25 ± 0.03 | +0.13 ± 0.02*(0.5) |
| 6(1) | 0.1 | −0.13 ± 0.04 | +0.22 ± 0.04 | +0.15 ± 0.05(0.5) |
|  | 0.3 | −0.12 ± 0.03 | +0.16 ± 0.02 | +0.07 ± 0.01**(5) |
| 79(3) | 0.1 | −0.11 ± 0.02 | +0.17 ± 0.02 | +0.12 ± 0.02(5) |
|  | 0.3 | −0.13 ± 0.03 | +0.19 ± 0.02 | +0.04 ± 0.02**(0.5) |
|  | 1.0 | −0.22 ± 0.03 | +0.22 ± 0.03 | +0.08 ± 0.01**(0.5) |
| Diltiazem hydrochloride | 0.1 | −0.12 ± 0.02 | +0.23 ± 0.02 | +0.15 ± 0.03(10) |
|  | 0.3 | −0.08 ± 0.03 | +0.16 ± 0.02 | +0.06 ± 0.02**(10) |
|  | 1.0 | −0.20 ± 0.04 | +0.22 ± 0.03 | +0.09 ± 0.02**(5) |
| Nifedipine | 0.03 | −0.16 ± 0.02 | +0.21 ± 0.04 | +0.17 ± 0.02(10) |
|  | 0.1 | −0.09 ± 0.02 | +0.18 ± 0.03 | +0.08 ± 0.02*(20) |

*,**Significantly different from respective control (*: $P < 0.05$, **: $P < 0.01$)
***It means the compound of Ex. 1(3) (hereinafter the same)

As shown in Table 4, the compounds obtained in Examples 1(3), 2(3), 6(1) and 79(3) exhibited a preventive effect on the ST elevation comparable to that of diltiazem hydrochloride.

TEST 4

Acute lethal toxicity

STD-ddY strain mice were used in groups of 10 animals each. The mortality was observed for 7 days after single oral or intraperitoneal administration of the compound obtained in Example 1(3) or 79(3). The $LD_{50}$ value of both the compounds was more than 4 g/kg for oral administration and more than 1 g/kg for intraperitoneal administration.

As is clear from the above experimental results, the compounds (I) and pharmaceutically acceptable salts thereof show potent calcium antagonistic activity with weak toxicity, and hence, are useful as a calcium antagonist for the prophylaxis and treatment of hypertension and/or ischemic heart disease. Particularly, 11-[4-[4-(4-fluorophenyl)-1-piperazinyl]butyrylamino]-6,11-dihydrodibenzo[b,e]thiepin, 11-[4-[4-(4-fluorophenyl)-1-piperazinyl]butyrylamino]-2-methyl-6,11-dihydrodibenzo[b,e]thiepin and some others and pharmaceutically acceptable salts thereof show longer duration of antihypertensive activity than that of the commercially available calcium antagonists, and hence, are useful as an antihypertensive agent with long lasting effect.

The compounds of the formula (I) and pharmaceutically acceptable salts thereof can be administered by oral, parenteral or intrarectal route, preferably by oral route. The clinical dose of the compounds (I) and pharmaceutically acceptable salts thereof may vary according to the kinds of the compounds, administration routes, severity of disease, age of patients, or the like, but is usually in the range of 0.01 to 20 mg per kg of body weight per day, preferably 0.1 to 5 mg per kg of body weight per day, in human. The dose may be divided and administered in two to several times per day.

The compounds of the formula (I) and pharmaceutically acceptable salts thereof are usually administered to patients in the form of a pharmaceutical composition which contains a non-toxic and effective amount of the compounds. The pharmaceutical composition is usually prepared by admixing the active compounds (I) or their salts with conventional pharmaceutical carrier materials which are unreactive with the active compounds (I) or their salts. Suitable examples of the carrier materials are lactose, glucose, mannitol, dextrin, cyclodextrin, starch, sucrose, magnesium aluminosilicate tetrahydrate, synthetic aluminum silicate, microcrystalline cellulose, sodium carboxymethylcellulose, hydroxypropylstarch, calcium carboxymethylcellulose, ion exchange resin, methylcellulose, gelatin, acacia, pullulan, hydroxypropylcellulose, low substituted hydroxypropylcellulose, hydroxypropyl methylcellulose, polyvinylpyrrolidone, polyvinyl alcohol, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, propylene glycol, water, or the like.

The pharmaceutical composition may be in the dosage form of tablets, capsules, granules, fine granules, powders, syrups, suspension, suppositories, injections, or the like. These preparations may be prepared by conventional methods. Liquid preparations may be prepared by dissolving or suspending the active compounds in water or other suitable vehicles, when used. Tablets, granules and fine granules may be coated in a conventional manner.

The pharmaceutical composition may contain as the active ingredient the compound of the formula (I) or its pharmaceutically acceptable salt in the ratio of 0.5% by weight or more, preferably 1 to 70% by weight, based upon the whole weight of the composition. The composition may further contain one or more other therapeutically active compounds.

BEST MODE FOR CARRYING OUT THE INVENTION

The present invention is illustrated by the following Examples and Reference Examples, but should not be construed to be limited thereto. The identification of the compounds is carried out by elementary analysis, mass spectrum, IR spectrum, NMR spectrum, and the like.

In Examples and Reference Examples, the following abbreviations may optionally be used.

Me: methyl
Et: ethyl
Pr: propyl
Bu: butyl
Ph: phenyl
A: ethanol
AC: acetone
AE: ethyl acetate
AN: acetonitrile
CH: chloroform
E: diethyl ether
H: n-hexane
IA: isopropyl alcohol
M: methanol
T: toluene

EXAMPLE 1

Preparation of
11-[4-[4-(4-fluorophenyl)-1-piperazinyl]butyrylamino]-6,11-dihydrodibenzo[b,e]thiepin (1) A mixture of 5.0 g of 11-(4-chlorobutyrylamino)-6,11-dihydrodibenzo[b,e]thiepin, 5.5 g of 1-(4-fluorophenyl)piperazine, 5.0 g of sodium iodide and 50 ml of dimethylformamide is stirred at 100° C. for 1.5 hours. After the reaction mixture is cooled to room temperature, 100 ml of 10% aqueous potassium carbonate solution is added and the solution is extracted with three 300-ml portions of chloroform. The combined extracts are washed successively with water and saturated aqueous sodium chloride solution, and dried over magnesium sulfate, and the chloroform is distilled off. The residue is chromatographed on silica gel with chloroform-methanol (100:3) to give 5.0 g of the title compound. m.p. 194°-194.5° C. (recrystallized from chloroform-n-hexane);

(2) The free base (2.38 g) obtained in (1) is dissolved in a mixture of 30 ml of chloroform and 100 ml of ethanol, and 100 ml of ethanol containing 0.5 ml of concentrated hydrochloric acid is added. The solution is concentrated under reduced pressure and to the residue are added 100 ml of ethanol and 50 ml of water. The crystals are precipitated and collected by filtration to give 2.16 g of the hydrochloride of the title compound. m.p. 234° C. (recrystallized from ethanol-water);

(3) The free base (4.4 g) obtained in (1) is dissolved in 40 ml of chloroform, and 10 ml of ethanol containing 1.2 g of maleic acid is added. The solution is concentrated under reduced pressure, and 30 ml of ethanol is added to the residue. The resulting solution is allowed to stand at room temperature for some time and the precipitated crystals are collected by filtration to give 5.29 g of the maleate of the title compound. m.p. 149°-150° C. (recrystallized from ethanol);

(4) The free base (2.0 g) obtained in (1) and 0.88 g of citric acid are dissolved in 50 ml of ethanol, and the solution is concentrated to a volume of about 10 ml under reduced pressure. The ethanolic solution is added with stirring to 200 ml of diethyl ether. The crystals are precipitated and collected by filtration to give 2.3 g of the citrate of the title compound. m.p. 104°-105° C. (recrystallized from ethanol-diethyl ether).

EXAMPLE 2

Preparation of
11-[4-[4-(4-fluorophenyl)-1-piperazinyl]butyrylamino]-2-methyl-6,11-dihydrodibenzo[b,e]thiepin (1) A mixture of 10 g of 11-(4-chlorobutyrylamino)-2-methyl-6,11-dihydrodibenzo[b,e]thiepin, 10 g of 1-(4-fluorophenyl)piperazine, 10 g of sodium iodide and 100 ml of dimethylformamide is stirred at 100° C. for 1.5 hours. After the reaction mixture is cooled to room temperature, 100 ml of 10% aqueous potassium carbonate solution is added and the solution is extracted with three 300-ml portions of chloroform. The combined extracts are treated in substantially the same manner as in Example 1(1) to give 9.2 g of the title compound. m.p. 205°-207° C. (recrystallized from ethyl acetate);

(2) The free base obtained in (1) is treated in substantially the same manner as in Example 1(2) to give the hydrochloride 9/4 hydrate of the title compound. m.p. 151°-153° C. (recrystallized from ethanol-water);

(3) The free base obtained in (1) is treated in substantially the same manner as in Example 1(4), using maleic acid instead of citric acid, to give the maleate of the title compound. m.p. 90°-95° C. (recrystallized from ethanol-diethyl ether);

(4) The free base (1.1 g) obtained in (1) is dissolved in 8 ml of chloroform, and 5 ml of ethanol containing 0.4 g of fumaric acid is added. The solution is concentrated under reduced pressure and to the residue are added 8 ml of ethanol and 16 ml of water. The resulting solution is allowed to stand at room temperature for some time and the precipitated crystals are collected by filtration to give 1.1 g of the hemifumarate hemihydrate of the title compound. m.p. 197° C. (decomp.) (recrystallized from ethanol-water);

(5) The free base (490 mg) obtained in (1) is dissolved in a mixture of 8 ml of chloroform, 8 ml of methanol and 2 ml of water, and 106 mg of methanesulfonic acid is added. The solution is concentrated under reduced pressure and to the residue are added 20 ml of ethanol and 10 ml of water. The precipitated crystals are collected by filtration to give 447 mg of the methanesulfonate ¾ hydrate of the title compound. m.p. 204° C. (decomp.) (recrystallized from ethanol-water);

(6) The free base obtained in (1) is treated in substantially the same manner as in Example 2(5), using phosphoric acid instead of methanesulfonic acid, to give the phosphate of the title compound. m.p. 224° C. (decomp.) (recrystallized from ethanol-water).

EXAMPLE 3

Preparation of
11-[5-(4-phenyl-1-piperazinyl)valerylamino]-6,11-dihydrodibenzo[b,e]thiepin (1) A mixture of 1.3 g of 11-(5-chlorovalerylamino)-6,11-dihydrodibenzo[b,e]thiepin, 1.5 g of 1-phenylpiperazine, 1.3 g of sodium iodide and 20 ml of dimethylformamide is stirred at 85° C. for 15 hours. After the reaction mixture is cooled to room temperature, 50 ml of 10% aqueous potassium carbonate solution is added and the solution is extracted with three 100-ml portions of toluene. The combined extracts are washed successively with water and saturated aqueous sodium chloride solution, and dried over magnesium sulfate, and the toluene is distilled off. The residue is chromatographed on silica gel with chloroform-methanol (100:3) to give 0.9 g of the title compound. m.p. 183°-184° C. (recrystallized from ethanol-n-hexane);

(2) The free base obtained in (1) is treated in substantially the same manner as in Example 1(4), using maleic acid instead of citric acid, to give the maleate of the title compound. m.p. 176°-177° C. (recrystallized from ethanol-diethyl ether)

EXAMPLES 4 TO 78

Various compounds listed in the following Table 5 are prepared in substantially the same manner as in Examples 1 to 3, using the corresponding starting materials.

TABLE 5

[Structure shown: thioxanthene-type tricyclic system with positions 1-10, S at position 5, CH at position 6, and substituent at position 11: —N(R₃)—CO(CH₂)ₙ—N(piperazine)N—R₄·Q; R₂ on upper ring, R₁ on lower ring]

| Ex. | n | $R_1$ | $R_2$ | $R_3$ | $R_4$ | Q | m.p. (°C.) (recryst. solvent) |
|-----|---|-------|-------|-------|-------|---|------|
| 4(1) | 1 | H | H | H | Ph | — | 162~164 (CH—H) |
| (2) | " | " | " | " | " | maleate.1/4 H₂O | 106~108 (M—E) |
| 5(1) | 2 | " | " | " | " | — | 185~188 (AE—A) |
| (2) | " | " | " | " | " | maleate.3/4 H₂O | 145~146 (CH—E) |
| 6(1) | 3 | " | " | " | " | — | 189~190 (T) |
| (2) | " | " | " | " | " | maleate | 142~143 (A—E) |
| 7(1) | 2 | " | " | " | CH₂Ph | — | 150~152 (T—H) |
| (2) | " | " | " | " | " | dimaleate.1/2 H₂O | 191~192 (M) |
| 8(1) | 3 | " | " | " | " | — | 142~143 (T) |
| (2) | " | " | " | " | " | dimaleate.3/4 H₂O | 190~191 (A) |
| 9(1) | 4 | " | " | " | " | — | 141~142 (T—H) |
| (2) | " | " | " | " | " | dimaleate.1/6 EtOH | 193~194 (A) |
| 10(1) | 2 | " | " | " | 4-F-C₆H₄ | — | 189~192 (T—H) |
| (2) | " | " | " | " | " | maleate | 172~175 (A) |
| 11(1) | 4 | " | " | " | " | 1/4 H₂O | 200~201 (CH—H) |
| 11(2) | 4 | " | " | " | " | maleate | 194~195 (A) |
| 12 | 3 | " | " | " | 4-F-C₆H₄-CH₂ | — | 167~168 (A—E) |
| 13 | " | " | " | " | 3-F-C₆H₄ | 1/4 H₂O | 146~148 (A—H) |
| 14 | " | " | " | " | 2-F-C₆H₄ | — | 151~152 (M—E) |
| 15 | " | " | " | " | 2-F-C₆H₄-CH₂ | — | 148~150 (CH—H) |

TABLE 5-continued
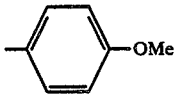
| Ex. | n | R₁ | R₂ | R₃ | R₄ | Q | m.p. (°C.) (recryst. solvent) |
|---|---|---|---|---|---|---|---|
| 16 | " | " | " | " | 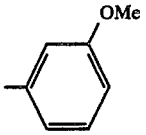 —OMe (para) | 1/4 H₂O | 193~195 (CH—H) |
| 17 | " | " | " | " | 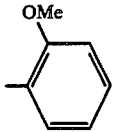 OMe (meta) | — | 105~108 (CH—E) |
| 18 | " | " | " | " | 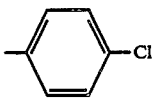 OMe (ortho) | 1/4 H₂O | 152~154 (CH—H) |
| 19 | " | " | " | " |  —Cl (para) | " | 216~217 (AE) |
| 20 | " | " | " | " | CH₂— 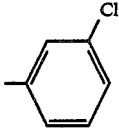 —Cl | dimaleate.1/4 H₂O | 184~185 (M—E) |
| 21 | " | " | " | " | 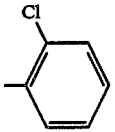 Cl (meta) | — | 215~217 (CH—H) |
| 22 | " | " | " | " | 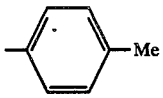 Cl (ortho) | — | 164~166 (CH—H) |
| 23 | " | " | " | " |  —Me (para) | 1/4 H₂O | 186~187 (CH—H) |
| 24 | " | " | " | " | CH₂— 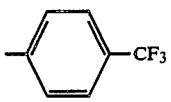 —Me | 1/2 H₂O | 129~130 (CH—H) |
| 25 | " | " | " | " | —⟨ ⟩—CF₃ | — | 228~230 (CH—H) |

TABLE 5-continued

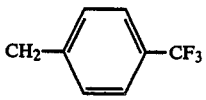

| Ex. | n | $R_1$ | $R_2$ | $R_3$ | $R_4$ | Q | m.p. (°C.) (recryst. solvent) |
|---|---|---|---|---|---|---|---|
| 26 | " | " | " | " | 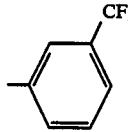 $CH_2$—⟨⟩—$CF_3$ | 1/2 $H_2O$ | 142~145 (CH—H) |
| 27 | " | " | " | " | 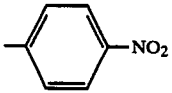 3-$CF_3$-phenyl | 1/4 $H_2O$ | 165~167 (CH—H) |
| 28 | 3 | " | " | " | 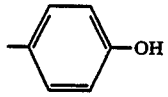 4-$NO_2$-phenyl | 1/4 $H_2O$ | 275~277 (CH) |
| 29 | " | " | " | " | 4-OH-phenyl | — | oil 473* |
| 30 | " | " | " | " | 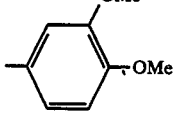 3,4-diOMe-phenyl | — | 190~191 (M—E) |
| 31 | " | " | " | Me | Ph | oxalate | 185~187 (M—E) |
| 32 | " | " | 3-Me | H | 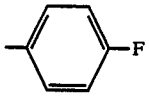 4-F-phenyl | — | 176~178 (AE) |
| 33 | " | " | 4-Me | " | " | — | 168~171 (AE) |
| 34 | " | " | 2-OMe | " | " | — | 198~201 (CH—AE) |
| 35 | " | " | 3-OMe | " | " | — | 177~180 (AE—E) |
| 36 | " | " | 4-OMe | " | " | — | 177~179 (AE) |
| 37 | " | " | 2-Br | " | " | 1/4 $H_2O$ | 196~198 (CH—AE) |
| 38 | " | " | 2-Cl | " | " | — | 196~198 (AE) |
| 39 | " | " | 3-Cl | " | " | 1/4 $H_2O$ | 186~189 (CH—AE) |
| 40 | " | " | 4-Cl | " | " | " | 181~183 (CH—AE) |
| 41 | " | " | 2-F | " | " | — | 198~200 (AE) |
| 42 | " | " | 3-F | " | " | 1/4 $H_2O$ | 189~190 (CH—AE) |
| 43 | " | " | 3-SMe | " | " | " | 188~190 (CH—AE) |
| 44 | " | 8-Cl | H | " | " | 1/2 $H_2O$ | 208~209 (CH—H) |
| 45 | " | 9-F | " | " | " | — | 210~212 (CH—H) |
| 46 | " | 8-OMe | " | " | " | 1/4 $H_2O$ | 191~194 (CH—H) |
| 47 | 3 | H | 2-Cl | H | 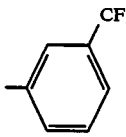 3-$CF_3$-phenyl | — | 155~157 (CH—H) |
| 48 | " | " | 2-Me | " | " | — | 176~177 (CH—H) |

TABLE 5-continued

| Ex. | n | R₁ | R₂ | R₃ | R₄ | Q | m.p. (°C.) (recryst. solvent) |
|---|---|---|---|---|---|---|---|
| 49 | " | " | " | " | 2-OMe-C₆H₄ | — | 190~192 (CH—H) |
| 50 | " | " | " | " | 4-Cl-C₆H₄ | — | 204~207 (CH—H) |
| 51 | " | " | " | " | 2-Cl-C₆H₄ | — | 188~190 (CH—A) |
| 52 | " | " | " | " | 2-F-C₆H₄ | — | 192~193 (CH—H) |
| 53 | " | " | " | " | CH₂CH=CHPh | dimaleate | 191~193 (A) |
| 54 | " | " | " | " | CH₂CH=CH-C₆H₄-4-F | dimaleate.1/2 H₂O | 190~192 (A) |
| 55 | 4 | " | " | " | CH₂CH=CHPh | dimaleate | 185~188 (A) |
| 56 | 3 | " | " | " | 2-pyridyl | — | 180~182 (CH—A) |
| 57 | " | " | 2-Et | " | 4-F-C₆H₄ | — | 214~216 (CH—A) |
| 58 | " | " | 2-i-Pr | " | " | — | 198~200 (CH—A) |
| 59 | " | " | 2-n-Bu | " | " | — | 204~206 (CH—A) |
| 60 | " | " | 2,3-Me₂ | " | " | — | 212~214 (CH—H) |
| 61 | " | " | 4-F | " | " | 1/4 H₂O | 220~222 (CH—H) |
| 62 | " | " | H | " | CH₂CH=CHPh | dimaleate.3/4 H₂O | 183~184 (A) |
| 63 | " | " | " | " | (CH₂)₃—Ph | dimaleate | 178~180 (A) |
| 64 | 3 | " | " | " | CH₂COPh | dimaleate | 156~157 (A) |
| 65 | " | " | " | " | CH₂CH(OH)Ph | 1/2 H₂O | 190~193 (A) |
| 66 | " | " | " | " | CHPh₂ | — | 180~181 (AE) |

TABLE 5-continued

[Structure: thioxanthene-type compound with numbered positions 1-10, S at position 5, C-11 bearing N-R3 and N—CO(CH2)n—N(piperazine)N—R4.Q, with R2 on upper ring and R1 on lower ring]

| Ex. | n | R₁ | R₂ | R₃ | R₄ | Q | m.p. (°C.) (recryst. solvent) |
|---|---|---|---|---|---|---|---|
| 67 | " | " | " | " | CH(4-F-C₆H₄)₂ | 1/4 H₂O | 183~184 (AE) |
| 68 | " | " | " | " | 1-naphthyl | — | 176~178 (AE) |
| 69(1) | " | " | " | " | 2-pyridyl | — | 155~157 (M—H) |
| (2) | " | " | " | " | " | citrate.2 H₂O | 102~108 (CH—E) |
| 70 | 2 | " | " | " | " | — | 160~163 (CH—AE) |
| 71 | 4 | " | " | " | " | — | 188~190 (CH—AC) |
| 72 | 3 | " | " | " | 2-(3-CO₂Et)pyridyl | 1/2 H₂O | 140~142 (CH—H) |
| 73 | " | " | " | " | 2-pyrimidinyl | — | 198~199 (CH—H) |
| 74 | " | " | " | " | 2-furoyl (CO-furan) | citrate.1/4 H₂O | 100~102 (A—E) |
| 75 | " | " | " | " | COPh | dioxalate | 232~234 (CH—M) |
| 76 | " | " | " | " | COOPh | citrate.1/2 H₂O | 110~112 (A—E) |
| 77 | " | " | " | " | SO₂—O—Ph | — | 95~100 (A—E) |
| 78 | " | " | " | " | SO₂-(4-Me-C₆H₄) | 3/4 H₂O | 108~110 (A—E) |

*m/z (M⁺) in mass spectrum

EXAMPLE 79

Preparation of
5-[4-[4-(4-fluorophenyl)-1-piperazinyl]butyrylamino]-
5H-dibenzo[a,d]cycloheptene (1) A mixture of 5.0 g of 5-(4-chlorobutyrylamino)-5H-dibenzo[a,d]cycloheptene, 5.8 g of 1-(4-fluorophenyl)piperazine, 5.0 g of sodium iodide and 50 ml of dimethylformamide is stirred at 100° C. for 1.5 hours. After the reaction mixture is cooled to room temperature, 100 ml of 10% aqueous potassium carbonate solution is added and the solution is extracted with three 300-ml portions of chloroform. The combined extracts are washed successively with water and saturated aqueous sodium chloride solution, and dried over magnesium sulfate, and the chloroform is distilled off. The residue is chromatographed on silica gel with chloroform-methanol (100:3) to give 5.4 g of the title compound. m.p. 233°-235° C. (recrystallized from chloroform-ethyl acetate);

(2) The free base obtained in (1) is treated in substantially the same manner as in Example 1(2) to give the hydrochloride of the title compound. m.p. 250°-253° C. (decomp.) (recrystallized from methanol);

(3) The free base obtained in (1) is treated in substantially the same manner as in Example 1(4), using maleic acid instead of citric acid, to give the maleate of the title compound. m.p. 164°-167° C. (recrystallized from ethanol-diethyl ether);

(4) The free base obtained in (1) is treated in substantially the same manner as in Example 1(4) to give the citrate of the title compound. m.p. 100°-105° C. (recrystallized from ethanol-diethyl ether);

(5) The free base obtained in (1) is treated in substantially the same manner as in Example 1(4), using tartaric acid instead of citric acid, to give the tartrate hydrate of the title compound. m.p. 107°-110° C. (recrystallized from ethanol-diethyl ether).

EXAMPLES 80 TO 128

Various compounds listed in the following Table 6 are prepared in substantially the same manner as in Example 79, using the corresponding starting materials.

TABLE 6

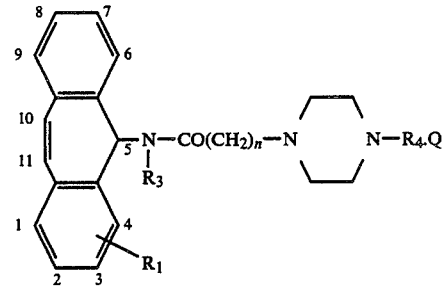

| Ex. | n | $R_1$ | $R_3$ | $R_4$ | Q | m.p.(°C.) (recryst. solvent) |
|---|---|---|---|---|---|---|
| 80(1) | 2 | H | H | Ph | ½$H_2O$ | 221~227 (CH—H) |
| (2) | " | " | " | " | maleate. ¾$H_2O$ | 114~116 (A—E) |
| 81(1) | 3 | " | " | " | — | 200~204 (CH—AE) |
| (2) | " | " | " | " | maleate | 159~161 (A—E) |
| 82(1) | 4 | " | " | " | ½$H_2O$ | 217~220 (CH—E) |
| (2) | " | " | " | " | maleate | 145~146 (CH—E) |
| 83 | 5 | " | " | " | ½$H_2O$ | 144~146 (CH—H) |
| 84(1) | 2 | " | " | $CH_2Ph$ | — | 170~172.5 (T—H) |
| 84(2) | " | " | " | " | dimaleate. ¼$H_2O$ | 192~195 (M) |
| 85(1) | 3 | " | " | " | — | 180~182 (M) |
| (2) | " | " | " | " | dihydrochloride. 3/2$H_2O$ | 175~178 (M—E) |
| 86(1) | 4 | " | " | " | ½$H_2O$ | 169~171 (T—H) |
| (2) | " | " | " | " | dimaleate | 191~192 (M) |
| 87 | 3 | " | " | $(CH_2)_2$—Ph | ½$H_2O$ | 204~205 (CH—H) |
| 88 | " | " | " | $(CH_2)_5$—Ph | dimaleate. ½$H_2O$ | 179~180 (M) |
| 89(1) | 2 | " | " | ⟨C6H4⟩—F | ½$H_2O$ | 238~240 (CH—H) |

TABLE 6-continued
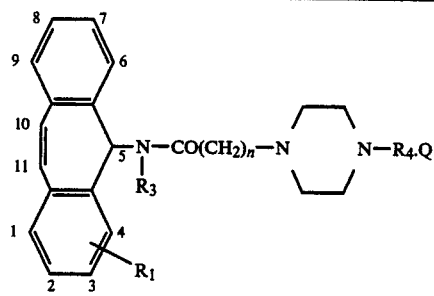
| Ex. | n | $R_1$ | $R_3$ | $R_4$ | Q | m.p.(°C.) (recryst. solvent) |
|---|---|---|---|---|---|---|
| (2) | " | " | " | " | maleate | 118~120 (CH—E) |
| 90(1) | 4 | " | " | " | ¼$H_2O$ | 235~236 (CH—H) |
| (2) | " | " | " | " | maleate. ½$H_2O$ | 195~196 (A) |
| 91 | 3 | " | " | $CH_2$-C$_6$H$_4$-F (para) | $H_2O$ | 184~187 (CH—H) |
| 92 | " | " | " | C$_6$H$_4$-F (meta) | ½$H_2O$ | 145~148 (A—E) |
| 93 | " | " | " | $CH_2$-C$_6$H$_4$-F (meta) | ¾$H_2O$ | 143~145 (CH—H) |
| 94 | " | " | " | C$_6$H$_4$-F (ortho) | — | 197~198 (CH—H) |
| 95 | " | " | " | $CH_2$-C$_6$H$_4$-F (ortho) | — | 194~197 (CH—H) |
| 96 | " | " | " | C$_6$H$_4$-CF$_3$ (para) | ½$H_2O$ | 171~172 (M—E) |
| 97 | " | " | " | $CH_2$-C$_6$H$_4$-CF$_3$ (para) | — | 168~170 (CH—H) |
| 98 | " | " | " | C$_6$H$_4$-CF$_3$ (meta) | — | 174~175 (M—E) |

TABLE 6-continued

Structure:

9,10-dihydroanthracen-9-yl with substituents at positions 1-11, bearing N(R$_3$)—CO(CH$_2$)$_n$—N(piperazine)N—R$_4$·Q, and R$_1$ on the lower ring.

| Ex. | n | R$_1$ | R$_3$ | R$_4$ | Q | m.p.(°C.) (recryst. solvent) |
|---|---|---|---|---|---|---|
| 99 | " | " | " | 4-MeO-C$_6$H$_4$— | oxalate. ¼H$_2$O | 194~196 (M—E) |
| 100 | " | " | " | 3-MeO-C$_6$H$_4$— | — | 135~138 (M) |
| 101 | " | " | " | 2-MeO-C$_6$H$_4$— | — | 180~182 (CH—H) |
| 102 | " | " | " | 3-HO-C$_6$H$_4$— | ½H$_2$O | 225~227 (M—E) |
| 103 | " | " | " | 2-HO-C$_6$H$_4$— | ¼H$_2$O | 210~211 (M) |
| 104 | " | " | " | 3,4-(MeO)$_2$-C$_6$H$_3$— | ½H$_2$O | 130~132 (M) |
| 105 | " | " | " | 3,4-(MeO)$_2$-C$_6$H$_3$—CH$_2$— | dimaleate. 3/2H$_2$O | 175~177 (M—E) |
| 106 | " | " | OMe | 4-F-C$_6$H$_4$— | oxalate | 168~170 (M—E) |
| 107 | " | 3-Me | H | " | — | 198~200 (CH—AE) |
| 108 | " | 3-Br | " | " | ¼H$_2$O | 220~222 (CH—AE) |
| 109 | " | 1-Cl | " | " | " | 223–224 (CH—AE) |
| 110 | " | 2-Cl | " | " | — | 181~183 (CH—AE) |
| 111 | " | 3-Cl | " | " | ¼H$_2$O | 228~229 |

TABLE 6-continued
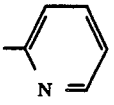
| Ex. | n | $R_1$ | $R_3$ | $R_4$ | Q | m.p.(°C.) (recryst. solvent) |
|---|---|---|---|---|---|---|
| 112 | " | 3-F | " | " | — | 233~234 (CH) |
| 113 | " | 3-CN | " | " | — | 239~240 (CH—AE) |
| 114 | " | 3-OMe | " | " | — | 143~145 (AE) |
| 115 | " | H | " | CH$_2$CH=CHPh | dimaleate. ¼H$_2$O | 204~205 (A) |
| 116 | 2 | " | " | 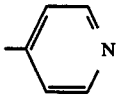 | ¼H$_2$O | 2190~221 (AE) |
| 117 | 3 | " | " | " | — | 171~173 (CH—E) |
| 118 | 4 | " | " | " | — | 193~196 (CH—AE) |
| 119 | 2 | " | Me | " | — | 180~183 (AE) |
| 120 | 3 | " | " | " | — | 130~132 (E) |
| 121 | 4 | " | " | " | — | 118~119 (E) |
| 122 | 3 | " | H | 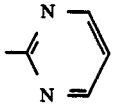 | ½H$_2$O | 235~237* (CH—AE) |
| 123 | " | " | " | 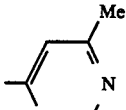 | — | 199~201 (CH—AE) |
| 124 | " | " | " | 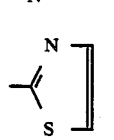 | ¼H$_2$O | 179~181 (CH—AE) |
| 125 | " | " | " | 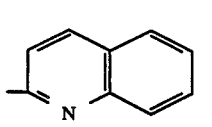 | — | 208~211 (CH—AE) |
| 126 | " | " | " |  | ¼H$_2$O | 196~206 (CH—AE) |
| 127 | " | " | " | COPh | oxalate | 246~250 (A—E) |

TABLE 6-continued

| Ex. | n | R₁ | R₃ | R₄ | Q | m.p.(°C.) (recryst. solvent) |
|---|---|---|---|---|---|---|
| 128 | " | " | Me | ![4-F-phenyl] | — | 114~116 (E—H) |

*Decomposition

EXAMPLE 129

Preparation of 11-[4-[4-(4-fluorophenyl)-1-piperazinyl]butyrylamino]-2-methyl-6,11-dihydrodibenzo[b,e]thiepin-5,5-dioxide:

A mixture of 2.0 g of 11-(4-chlorobutyrylamino)-2-methyl-6,11-dihydrodibenzo[b,e]thiepin-5,5-dioxide, 2.0 g of 1-(4-fluorophenyl)piperazine, 2.0 g of sodium iodide and 20 ml of dimethylformamide is stirred at 100° C. for one hour. After the reaction mixture is cooled to room temperature, 100 ml of 10% aqueous potassium carbonate solution is added and the solution is extracted with three 300-ml portions of chloroform. The combined extracts are washed successively with water and saturated aqueous sodium chloride solution, and dried over magnesium sulfate, and the chloroform is distilled off. The residue is recrystallized from chloroform-diethyl ether to give 2.1 g of the title compound, m.p. 163°–165° C.

EXAMPLE 130

Preparation of 11-[4-(4-cinnamyl-1-piperazinyl)butyrylamino]-2-methyl-6,11-dihydrodibenzo[b,e]thiepin-5,5-dioxide The title compound is prepared in substantially the same manner as in Example 129 using the corresponding starting materials, and the product is converted into the maleate thereof in a usual manner to give the dimaleate hemihydrate of the title compound. m.p. 174°–176° C. (recrystallized from ethanol)

EXAMPLES 131 TO 141

Various compounds listed in the following Table 7 are prepared in substantially the same manner as in Examples 1 to 3, 79 and 129, using the corresponding starting materials.

TABLE 7

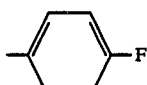

| Ex. | YZ | a | R₄ | Q | m.p. (°C.) (recryst. solvent) |
|---|---|---|---|---|---|
| 131(1) | —CH₂CH₂— | 2 | Ph | — | 208~210 (CH—T) |
| (2) | " | " | " | maleate.1/4 H₂O | 167~169 (A—E) |
| 132(1) | " | " | ![4-F-phenyl] | — | 213~215 (CH—AE) |
| (2) | " | " | " | maleate | 170~172 (A—E) |
| 133(1) | " | " | CH₂Ph | — | 172~174 (AE) |
| (2) | " | " | " | dimaleate.1/2 H₂O | 197~199 (CH—A) |

TABLE 7-continued

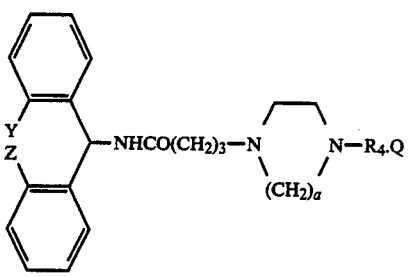

| Ex. | YZ | a | R4 | Q | m.p. (°C.) (recryst. solvent) |
|---|---|---|---|---|---|
| 134 | " | " | ![pyridyl] | — | 192~195 (AE) |
| 135 | —CH—CH—\\CH2/ | " | ![4-F-phenyl] | 1/4 H2O | 275~282 (CH—AE) |
| 136 | —SCH2—↓O | " | " | " | 181~182 (M—E) |
| 137* | " | " | " | oxalate | 157~160 (A—E) |
| 138 | —SCH2—↙↘O O | " | " | oxalate.1/2 MeOH | 222~223 (M—E) |
| 139 | " | " | CH2CH=CHPh | dimaleate.1/2 H2O | 175~176 (A) |
| 140 | —SCH2— | 3 | ![CH2-4-F-phenyl] | dioxalate.1/4 H2O | 191~194 (M) |
| 141 | —CH=CH— | " | ![pyridyl] | 1/4 H2O | 192~195 (CH—AE) |

*Stereoisomer of the compound of Example 136.

EXAMPLE 142

Preparation of
11-[4-[4-(4-fluorophenyl)-1-piperazinyl]butyrylamino]-6,11-dihydrodibenzo[b,e]thiepin (1) A mixture of 2.3 g of 11-amino-6,11-dihydrodibenzo[b,e]thiepin, 2.9 g of 4-[4-(4-fluorophenyl)-1-piperazinyl]butyric acid, 2.3 g of dicyclohexylcarbodiimide and 50 ml of methylene chloride is stirred at room temperature for 15 hours. After removal of the precipitated crystals by filtration, the filtrate is concentrated under reduced pressure. The residue is recrystallized from chloroform-n-hexane to give 1.9 g of the title compound, m.p. 194°–194.5° C.;

(2) The free base obtained in (1) is treated in substantially the same manner as in Example 1(2) to give the hydrochloride of the title compound. m.p. 234° C. (recrystallized from ethanol-water);

(3) The free base obtained in (1) is treated in substantially the same manner as in Example 1(3) to give the maleate of the title compound. m.p. 149°–150° C. (recrystallized from ethanol);

(4) The free base obtained in (1) is treated in substantially the same manner as in Example 1(4) to give the citrate of the title compound. m.p. 104°–105° C. (recrystallized from ethanol-diethyl ether).

EXAMPLE 143

Preparation of
11-[4-[4-(4-fluorophenyl)-1-piperazinyl]butyrylamino]-2-methyl-6,11-dihydrodibenzo[b,e]thiepin (1) A mixture of 2.4 g of 11-amino-2-methyl-6,11-dihydrodibenzo[b,e]thiepin, 2.9 g of 4-[4-(4-fluorophenyl)-1-piperazinyl]butyric acid, 2.3 g of dicyclohexylcarbodiimide and 50 ml of methylene chloride is stirred at room temperature for 15 hours. After removal of the precipitated crystals by filtration, the filtrate is concentrated under reduced pressure. The residue is recrystallized from ethyl acetate to give 2.0 g of the title compound, m.p. 205°–207° C.

(2) The free base obtained in (1) is treated in substantially the same manner as in Example 1(2) to give the hydrochloride 9/4 hydrate of the title compound. m.p. 151°-153° C. (recrystallized from ethanol-water);

(3) The free base obtained in (1) is treated in substantially the same manner as in Example 1(4), using maleic acid instead of citric acid, to give the maleate of the title compound. m.p. 90°-95° C. (recrystallized from ethanol-diethyl ether);

(4) The free base obtained in (1) is treated in substantially the same manner as in Example 2(4) to give the hemifumarate hemihydrate of the title compound. m.p. 197° C. (decomp.) (recrystallized from ethanol-water);

(5) The free base obtained in (1) is treated in substantially the same manner as in Example 2(5) to give the methanesulfonate 3/4 hydrate of the title compound. m.p. 204° C. (decomp.) (recrystallized from ethanol-water);

(6) The free base obtained in (1) is treated in substantially the same manner as in Example 2(6) to give the phosphate of the title compound. m.p. 224° C. (decomp.) (recrystallized from ethanol-water).

EXAMPLE 144

Preparation of 5-[4-[4-(4-fluorophenyl)-1-piperazinyl]butyrylamino]-N-methyl-5H-dibenzo[a,d]cycloheptene A mixture of 1.5 g of 4-[4-(4-fuluorophenyl)-1-piperazinyl]butyric acid, 1.3 g of dicyclohexylcarbodiimide and 20 ml of chloroform is stirred at 0° C. for one hour, and 1.3 g of 5-methylamino-5H-dibenzo[a,d]cycloheptene is added and the mixture is stirred at room temperature for 16 hours. After removal of the precipitated crystals by filtration, the filtrate is concentrated under reduced pressure. The residue is chromatographed on silica gel with chloroform to give 1.2 g of the title compound. m.p. 114°-116° C. (recrystallized from diethyl ether-n-hexane).

EXAMPLES 145 TO 282

The products obtained in Examples 3 to 127 and 129 to 141 are prepared in substantially the same manner as in Examples 142 to 144, using the corresponding starting materials.

EXAMPLE 283

Preparation of 5-[4-[4-(4-fluorophenyl)-1-piperazinyl]butyrylamino-5H-dibenzo[a,d]cycloheptene (1) A mixture of 200 mg of 5H-dibenzo[a,d]cyclohepten-5-ol, 300 mg of 4-[4-(4-fluorophenyl)-1-piperazinyl]butyramide and 8 ml of acetic acid is stirred at 70° C. for 20 hours. The acetic acid is distilled off under reduced pressure and 100 ml of chloroform is added to the residue. The solution is washed successively with 10% aqueous potassium carbonate solution, water and saturated aqueous sodium chloride solution, and dried over magnesium sulfate, and the chrloroform is distilled off. The residue is chromatographed on silica gel with chloroform-methanol (100:3) to give 250 mg of the title compound. m.p. 233°-235° C. (recrystallized from chloroform-n-hexane);

(2) The free base obtained in (1) is treated in substantially the same manner as in Example 1(2) to give the hydrochloride of the title compound. m.p. 250°-253° C. (decomp.) (recrystallized from methanol);

(3) The free base obtained in (1) is treated in substantially the same manner as in Example 1(4), using maleic acid instead of citric acid, to give the maleate of the title compound. m.p. 164°-167° C. (recrystallized from ethanol-diethyl ether);

(4) The free base obtained in (1) is treated in substantially the same manner as in Example 1(4) to give the citrate of the title compound. m.p. 100°-105° C. (recrystallized from ethanol-diethyl ether);

(5) The free base obtained in (1) is treated in substantially the same manner as in Example 1(4), using tartaric acid instead of citric acid, to give the tartrate hydrate of the title compound. m.p. 107°-110° C. (recrystallized from ethanol-diethyl ether).

EXAMPLES 284 TO 333

The products obtained in Examples 80 to 128 and 141 are prepared in substantially the same manner as in Example 283, using the corresponding starting materials.

EXAMPLE 334

Preparation of 11-[4-[4-(4-fluorophenyl)-1-piperazinyl]butyrylamino]-6,11-dihydrodibenzo[b,e]thiepin-5-oxide-A and -B (separation of the diastereomers)

11-[4-[4-(4-fluorophenyl)-1-piperazinyl]butyrylamino]-6,11-dihydrodibenzo[b,e]thiepin (3.0 g) is dissolved in 50 ml of dioxane, and a solution of 5 g of sodium metaperiodate in 10 ml of water is added. After the mixture is stirred at room temperature for one hour, it is washed successively with 10% aqueous sodium thiosulfate solution, water and saturated aqueous sodium chloride solution, and dried over magnesium sulfate. After removal of the solvent under reduced pressure, the residue is chromatographed on silica gel with chloroform-methanol (100:3). The first eluate affords 2.0 g of 11-[4-[4-(4-fluorophenyl)-1-piperazinyl]butyrylamino]-6,11-dihydrodibenzo[b,e]thiepin-5-oxide-A (hereinafter referred to as the Stereoisomer A) and the latter eluate affords 1.1 g of 11-[4-[4-(4-fluorophenyl)-1-piperazinyl]butyrylamino]-6,11-dihydrodibenzo[b,e]thiepin-5-oxide-B (hereinafter referred to as the Stereoisomer B).

The Stereoisomer A is recrystallized from methanol-diethyl ether to show m.p. 181°-182° C. and the oxalate of the Stereoisomer B is recrystallized from ethanol-diethyl ether to show m.p. 157°-160° C.

REFERENCE EXAMPLE 1

Preparation of 11-(5-chlorovalerylamino)-6,11-dihydrodibenzo[b,e]thiepin

A mixture of 8.8 g of 11-amino-6,11-dihydrodibenzo[b,e]thiepin, 6.0 g of 5-chlorovaleryl chloride and 100 ml of dioxane is heated with stirring under reflux for 15 hours. The solvent is distilled off under reduced pressure. The residue is recrystallized from ethanol to give 12.5 g of the title compound. m.p. 155°-156° C.

REFERENCE EXAMPLES 2 TO 35

Various compounds listed in the following Tables 8 to 10 are prepared in substantially the same manner as in Reference Example 1, using the corresponding starting materials.

Table 8

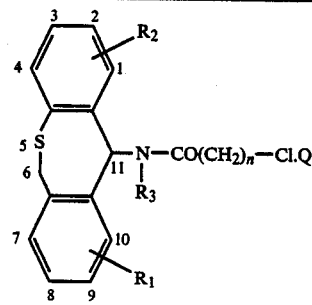

| Ref. Ex. | n | R₁ | R₂ | R₃ | Q | m.p.(°C.) (recryst. solvent) or mass spectrum |
|---|---|---|---|---|---|---|
| 2 | 1 | H | H | H | — | 187~189 (CH—H) |
| 3 | 2 | " | " | " | 1/5 EtOH | 177~177.5 (A) |
| 4 | 3 | " | " | " | — | 189~190 (A) |
| 5 | " | " | " | Me | — | oil; 345* |
| 6 | " | " | 2-Me | H | — | 188~190 (AE) |
| 7 | " | " | 3-Me | " | — | 174~176 (AE) |
| 8 | " | 3 | 4-Me | H | — | 179~182 (AE) |
| 9 | " | " | 2-OMe | " | — | 170~172 (AE) |
| 10 | " | " | 3-OMe | " | — | 176~178 (AE) |
| 11 | " | " | 4-OMe | " | — | 196~198 (AE) |
| 12 | " | " | 2-Br | " | 1/4 H₂O | 204~207 (CH—AE) |
| 13 | " | " | 2-Cl | " | — | 203~205 (AE) |
| 14 | " | " | 3-Cl | " | 1/4 H₂O | 193~196 (CH—AE) |
| 15 | " | " | 4-Cl | " | " | 208~210 (CH) |
| 16 | " | " | 2-F | " | — | 187~189 (AE) |
| 17 | " | " | 3-F | " | 1/4 H₂O | 210~212 (CH) |
| 18 | " | " | 3-SMe | " | — | 160~162 (CH—AE) |
| 19 | " | 8-Cl | H | " | — | oil; 365 |
| 20 | " | 9-F | " | " | — | oil; 349 |
| 21 | " | 8-OMe | " | " | — | oil; 361 |

*m/z (M⁺) (hereinafter the same)

TABLE 9

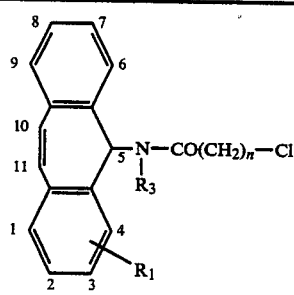

| Ref. Ex. | n | R₁ | R₃ | m.p.(°C.)(recryst. solvent) or mass spectrum |
|---|---|---|---|---|
| 22 | 2 | H | H | 220~223(A—H) |
| 23 | 3 | " | " | 220~233(T) |
| 24 | 4 | " | " | 221~222(CH) |
| 25 | 5 | H | H | oil; 339* |
| 26 | 3 | " | OMe | oil; 341 |
| 27 | " | 3-Me | H | 207~210(CH—AE) |
| 28 | " | 3-Br | " | 210~212(CH—AE) |
| 29 | " | 1-Cl | " | 230~233(CH) |
| 30 | " | 2-Cl | " | 229~231(AE) |
| 31 | " | 3-Cl | " | 222~225(CH) |
| 32 | " | 3-F | " | 219~221(CH) |
| 33 | " | 3-CN | " | 265~267(AE) |

*m/z (M⁺) (hereinafter the same)

TABLE 10

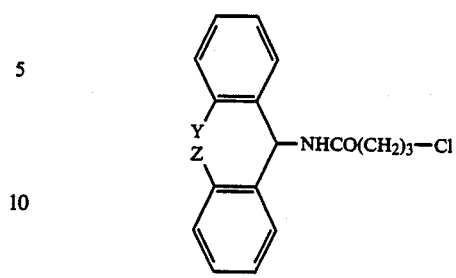

| Ref. Ex. | YZ | m.p.(°C.)(recryst. solvent) |
|---|---|---|
| 34 | —CH₂CH₂— | 220-222 (T) |
| 35 | —CH——CH— \ / CH₂ | 264-267 (CH—AE) |

REFERENCE EXAMPLE 36

Preparation of 11-(4-chlorobutyrylamino)-2-methyl-6,11-dihydrodibenzo[b,e]thiepin-5,5-dioxide 11-(4-Chlorobutyrylamino)-2-methyl-6,11-dihydrodibenzo[b,e]thiepin (5.0 g) is dissolved in 100 ml of chloroform, and 12 g of m-chloroperbenzoic acid is added under ice-cooling. The mixture is stirred at 0° C. for one hour and then washed successively with 10% aqueous sodium hydroxide solution, water and saturated aqueous sodium chloride solution, and dried over magnesium sulfate. The chloroform is distilled off and the residue is recrystallized from methanol to give 5.1 g of the title compound, m.p. 203°-204° C.

REFERENCE EXAMPLE 37

Preparation of 11-(4-chlorobutyrylamino)-6,11-dihydrodibenzo[b,e]-thiepin-5,5-dioxide The title compound is prepared in substantially the same manner as in Reference Example 36, using the corresponding starting material. m.p. 215°-227° C. (recrystallized from methanol).

EXAMPLE 335

| | per 1,000 tablets |
|---|---|
| 11-[4-[4-(4-Fluorophenyl)-1-piperazinyl]-butyrylamino]-6,11-dihydrodibenzo[b,e]-thiepin maleate | 10 g |
| Corn starch | 33 g |
| Lactose | 70 g |
| Microcrystalline cellulose | 30 g |
| Hydroxypropylcellulose | 5 g |
| Light anhydrous silicic acid | 1 g |
| Magnesium stearate | 1 g |

The above components are blended, granulated and made into 1,000 tablets each weighing 150 mg by a conventional method. The tablets are further coated with hydroxypropyl methylcellulose, talc, titanium dioxide, and sorbitan monooleate in a customary manner. There are obtained 1,000 film coated tablets.

EXAMPLE 336

| | per 1,000 capsules |
|---|---|
| 11-[4-[4-(4-Fluorophenyl)-1-piperazinyl]-butyrylamino]-2-methyl-6,11-dihydrodibenzo-[b,e]thiepin | 20 g |
| Corn starch | 42 g |
| Lactose | 10 g |
| Microcrystalline cellulose | 25 g |
| Hydroxypropylcellulose | 2 g |
| Light anhydrous silicic acid | 0.5 g |
| Magnesium stearate | 0.5 g |

The above components are blended, granulated and filled into 1,000 capsules by a conventional method.

EXAMPLE 337

| | fine granules |
|---|---|
| 11-[4-[4-(4-Fluorophenyl)-1-piperazinyl]-butyrylamino]-2-methyl-6,11-dihydrodibenzo-[b,e]thiepin hemifumarate hemihydrate | 100 g |
| Corn starch | 200 g |
| Lactose | 660 g |
| Light anhydrous silicic acid | 10 g |
| Hydroxypropylcellulose | 30 g |

The above components are blended and made into fine granules by a conventional method. The fine granules are further coated with dimethylaminoethyl acrylate-methacrylate copolymer, macrogol, titanium dioxide, talc and magnesium stearate.

INDUSTRIAL APPLICABILITY

The compounds of the formula (I) and pharmaceutically acceptable salts thereof are useful as a calcium antagonist for the prophylaxis and treatment of hypertension and/or ischemic heart disease in mammals including human.

What is claimed is:

1. A compound of the formula:

[Structural formula showing a dibenzothiepin-like tricyclic system with Y—Z bridge, substituent $R_1$, and side chain —NHCO—(CH$_2$)$_n$—N(piperazinyl)—$R_4$]

wherein
n is 2, 3 or 4;
Y—Z is $$-CH_2S-, \quad \downarrow (O)_d$$

—CH=CH— or —CH$_2$CH$_2$—,
d is 0, 1 or 2;
$R_1$ is hydrogen, halogen, $C_{1-3}$ alkyl or $C_{1-3}$ alkoxy, and $R_4$ is phenyl, phenyl-$C_{1-3}$ alkyl, phenyl-$C_{3-5}$ alkenyl or pyridyl, wherein the phenyl and phenyl moiety in $R_4$ above definition is either unsubstituted or substituted by halogen or trifluoromethyl, or a pharmaceutically acceptable salt thereof.

2. The compound according to claim 1, wherein n is 3; $R_1$ is hydrogen, fluorine, methyl or methoxy; $R_4$ is phenyl, phenyl substituted by halogen or trifluoromethyl, benzyl, cinnamyl or pyridyl, or a pharmaceutically acceptable salt thereof.

3. The compound according to claim 1, wherein n is 3; Y—Z is $$-CH_2S-; \quad \downarrow (O)_d$$

$R_1$ is hydrogen, fluorine, methyl or methoxy; $R_4$ is phenyl, or 2 or 4-fluorophenyl, 2 or 4-chlorophenyl, cinnamyl, 3-trifluoromethylphenyl or 2-pyridyl, or a pharmaceutically acceptable salt thereof.

4. The compound according to claim 1, wherein n is 3; Y—Z is —CH=CH—; $R_1$ is hydrogen or fluorine, $R_4$ is 4-fluorophenyl or cinnamyl, or a pharmaceutically acceptable salt thereof.

5. The compound according to claim 1, which is 11-[4-[4-(4-fluorophenyl)-1-piperazinyl]butyrylamino]-6,11-dihydrodibenzo[b,e]thiepin, or a pharmaceutically acceptable salt thereof.

6. The compound according to claim 1, which is 11-[4-[4-(4-fluorophenyl)-1-piperazinyl]butyrylamino]-2-methyl-6,11-dihydrodibenzo[b,e]thiepin, or a pharmaceutically acceptable salt thereof.

7. The compound according to claim 1, which is 11-[4-[4-(4-fluorophenyl)-1-piperazinyl]butyrylamino]-6,11-dihydrodibenzo[b,e]thiepin-5-oxide, or a pharmaceutically acceptable salt thereof.

8. The compound according to claim 1, which is 11-[4-[4-(4-fluorophenyl)-1-piperazinyl]-butyrylamino]-6,11-dihydrodibenzo[b,e]thiepin-5,5-dioxide, or a pharmaceutically acceptable salt thereof.

9. The compound according to claim 1, which is 5-[4-[4-(4-fluorophenyl)-1-piperazinyl]butyrylamino]-5H-dibenzo[a,d]cycloheptene, or a pharmaceutically acceptable salt thereof.

10. The compound according to claim 1, which is 3-fluoro-11-[4-[4-(4-fluorophenyl)-1-piperazinyl]-butyrylamino]-6,11-dihydrodibenzo[b,e]thiepin or a pharmaceutically acceptable salt thereof.

11. A pharmaceutical composition having a calcium antagonistic activity, which comprises as an active ingredient an effective amount of a compound as set forth in claim 1, or a pharmaceutically acceptable salt thereof and a pharmaceutically acceptable carrier.

12. The pharmaceutical composition according to claim 11, wherein the active ingredient is a compound as set forth in claim 2, or a pharmaceutically acceptable salt thereof.

13. The pharmaceutical composition according to claim 11, wherein the active ingredient is a compound as set forth in claim 3, or a pharmaceutically acceptable salt thereof.

14. The pharmaceutical composition according to claim 11, wherein the active ingredient is a compound as set forth in claim 4, or a pharmaceutically acceptable salt thereof.

15. The pharmaceutical composition according to claim 11, wherein the active ingredient is a compound as set forth in claim 5, or a pharmaceutically acceptable salt thereof.

16. The pharmaceutical composition according to claim 11, wherein the active ingredient is a compound as set forth in claim 6, or a pharmaceutically acceptable salt thereof.

17. The pharmaceutical composition according to claim 11, wherein the active ingredient is a compound as set forth in claim 7, or a pharmaceutically acceptable salt thereof.

18. The pharmaceutical composition according to claim 11, wherein the active ingredient is a compound as set forth in claim 8, or a pharmaceutically acceptable salt thereof.

19. The pharmaceutical composition according to claim 11, wherein the active ingredient is a compound as set forth in claim 9, or a pharmaceutically acceptable salt thereof.

20. The pharmaceutical composition according to claim 11, wherein the active ingredient is a compound as set forth in claim 10, or a pharmaceutically acceptable salt thereof.

* * * * *

UNITED STATES PATENT AND TRADEMARK OFFICE
CERTIFICATE OF CORRECTION

PATENT NO. : 4,749,703
DATED     : June 7, 1988
INVENTOR(S) : Hitoshi Uno, et al.

It is certified that error appears in the above-identified patent and that said Letters Patent is hereby corrected as shown below:

Column 2, line 36: "compposition" should read as --composition--

Column 4, line 22: "[4[4-(" should read as --[4-[4-(--

Column 27, line 5: "cycloheptene" should read as --cycloheptene:--

Column 33, Example 116: "$\frac{1}{4}H_2O$ 2190" should read as --$\frac{1}{4}H_2O$ 219--

Signed and Sealed this

Ninth Day of May, 1989

*Attest:*

DONALD J. QUIGG

*Attesting Officer*         *Commissioner of Patents and Trademarks*